United States Patent
Kim et al.

(12) United States Patent    (10) Patent No.: US 7,659,825 B2
Kim et al.    (45) Date of Patent: Feb. 9, 2010

(54) APPARATUS AND METHOD FOR CALCULATING LIFE EXPECTANCY IN MOBILE COMMUNICATION TERMINAL

(75) Inventors: Sun-Il Kim, Suwon-si (KR); Hee-Deog Kim, Seongnam-si (KR)

(73) Assignee: Samsung Electronics Co., Ltd. (KR)

( * ) Notice: Subject to any disclaimer, the term of this patent is extended or adjusted under 35 U.S.C. 154(b) by 206 days.

(21) Appl. No.: 11/731,547

(22) Filed: Mar. 30, 2007

(65) Prior Publication Data

US 2007/0241912 A1    Oct. 18, 2007

(30) Foreign Application Priority Data

Apr. 5, 2006    (KR) .................. 10-2006-0030806

(51) Int. Cl.
*G08B 23/00*    (2006.01)

(52) U.S. Cl. .................................................. 340/573.1
(58) Field of Classification Search ............. 340/573.1, 340/691.6, 323 R; 600/300
See application file for complete search history.

(56) References Cited

U.S. PATENT DOCUMENTS

| | | | |
|---|---|---|---|
| 6,059,724 A * | 5/2000 | Campell et al. | 600/300 |
| 7,302,398 B2 * | 11/2007 | Ban et al. | 705/2 |
| 2005/0010435 A1 * | 1/2005 | Kato et al. | 705/2 |
| 2005/0038332 A1 * | 2/2005 | Saidara et al. | 600/347 |
| 2005/0209528 A1 * | 9/2005 | Sato et al. | 600/547 |

* cited by examiner

*Primary Examiner*—Phung Nguyen
(74) *Attorney, Agent, or Firm*—The Farrell Law Firm, LLP

(57) ABSTRACT

An apparatus and method for calculating life expectancy in mobile communication terminal are provided that include inputting user data when a life expectancy program menu is selected, calculating the life expectancy using the inputted user data, and displaying a calculated result on a display unit.

19 Claims, 6 Drawing Sheets

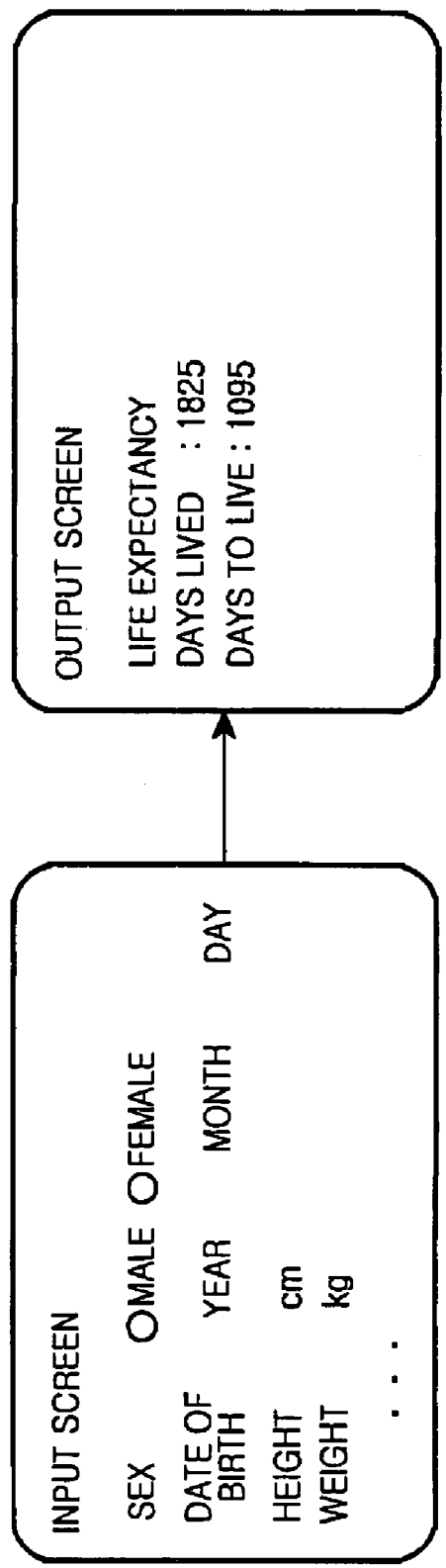

APPARATUS AND METHOD FOR CALCULATING LIFE EXPECTANCY IN MOBILE COMMUNICATION TERMINAL

PRIORITY

This application claims priority under 35 U.S.C. § 119 to an application filed in the Korean Intellectual Property Office on Apr. 5, 2006 and assigned Serial No. 2006-30806, the contents of which are incorporated herein by reference.

BACKGROUND OF THE INVENTION

1. Field of the Invention

The present invention relates generally to a mobile communication terminal, and in particular, to an apparatus and method for calculating life expectancy using life expectancy data.

2. Description of the Related Art

The use of mobile communication terminals is widespread because of their portability. Accordingly, service providers (and terminal manufacturers) are competitively developing mobile communication terminals with more convenient functions in order to attract potential users. Mobile communication terminals provide a variety of additional functions and services, such as a credit card payment service, a bus and subway fare payment service, a clock function, a camera function, and an MPEG Layer 3 (MP3) function, in addition to basic telephone communication functions. Thus, mobile communication terminals have become necessary accessories that accompany users at home, in the workplace, and wherever they go.

Within the past three to four years well-being was introduced as an important concept and well-being has in recent years become an important part of our culture. Well-being considerations have influenced our lifestyles and have become a criteria for basing our decisions on all aspects of life. Thus, well-being mobile communication terminals, which will bring forth a digital well-being era and a full-fledged mobile health care era, are being developed.

New concept mobile phones emphasizing well-being functions are being developed and introduced. Examples include a biophone that measures physiological signals (e.g., an electrocardiogram, blood pressure, and pulse rate), a glycosuria phone that measures and manages glycosuria, a stress phone that automatically checks a stress index, and a diet phone that measures calorie intake and provides dieting contents. The active pursuit of a happy well-being lifestyle can beg encouraged through mobile phones products that emphasize a sound mind and a sound body.

When well-being functions are added to the functions of a mobile phone, efficiency of the well-being functions will be highly increased. Therefore, a variety of methods for managing users' health are needed in addition to the well-being functions that already exist.

SUMMARY OF THE INVENTION

An object of the present invention is to substantially solve at least the above problems and/or disadvantages and to provide at least the advantages below. Accordingly, an object of the present invention is to provide an apparatus and method for calculating factors that improve or are material to life expectancy in a mobile communication terminal.

According to one aspect of the present invention, a method for calculating a life expectancy in a mobile communication terminal includes inputting user data when a life expectancy program menu is selected; calculating the life expectancy using the inputted user data; and displaying a calculated result on a display unit.

According to another aspect of the present invention, an apparatus for calculating a life expectancy in a mobile communication terminal includes a keypad for inputting a user data; a control unit for receiving the user data, calculating the life expectancy using the inputted user data, and displaying a calculated result; and a display unit for displaying the calculated life expectancy result, when a life expectancy program menu is selected.

BRIEF DESCRIPTION OF THE DRAWINGS

The above and other objects, features and advantages of the present invention will become more apparent from the following detailed description when taken in conjunction with the accompanying drawings in which:

FIGS. 3A and 3B are examples showing a life expectancy calculation result according to inputted life expectancy calculation data in the mobile communication terminal according to the present invention;

DETAILED DESCRIPTION OF THE PREFERRED EMBODIMENTS

Preferred embodiments of the present invention will be described herein below with reference to the accompanying drawings. In the following description, well-known functions or constructions are not described in detail to avoid obscuring the invention with unnecessary detail.

Figure 1:
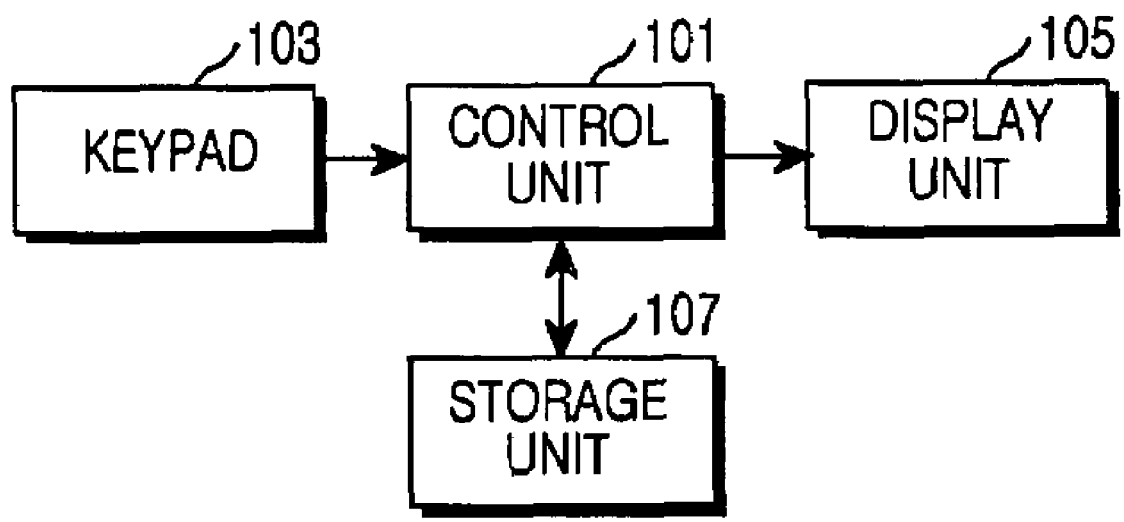
FIG. 1 is a block diagram of a mobile communication terminal according to the present invention.

FIG. 1 is a block diagram of a mobile communication terminal according to the present invention. Examples of the mobile communication terminal include cellular phones, Personal Communication System (PCS) terminals, Personal Data Assistants (PDAs), and International Mobile Telecommunication-2000 (IMT-2000) terminals. The following descriptions will be made with reference to a general structure of the above terminals. The mobile communication terminal includes a control unit (e.g., microprocessor unit (MPU)) 101, a keypad 103, display unit 105, and a storage unit 107.

Referring to FIG. 1, the control unit 101 controls an overall operation of the mobile terminal. For example, the control unit 101 processes and controls voice communication and data communication. In addition to the general functions, the control unit 101 calculates life expectancy according to data inputted through user manipulation of keys, and processes a function for connecting a variety of programs according to a calculated result.

The keypad 103 includes numeric keys of digits 0-9 and a plurality of function keys, such as a Menu key, a Cancel (Delete) key, a Confirmation key, a Talk key, an End key, an Internet connection key, and Navigation keys (or direction keys) (▲/▼/◄/►) to provide key input data corresponding to keys pressed by a user to the controller 101. Another input means such as a touch pad can also be used. The display unit 105 displays status data generated during operations, numerals and characters, moving pictures and still pictures, stored messages, and so on. A color TFT LCD may be used for the display unit 105.

The storage unit (memory unit) 107 includes a Read Only Memory (ROM), a Random Access Memory (RAM), and a flash ROM. The ROM stores microcodes of a program for the controlling and processing of the control unit 101 and a variety of reference data. The storage unit 107 stores a program for connecting a variety of programs according to the result of life expectancy calculated by the control unit 101. The RAM is a working memory of the control unit 101 and temporarily stores data generated during operations. The flash RAM stores a variety of updatable data.

Figure 2A:
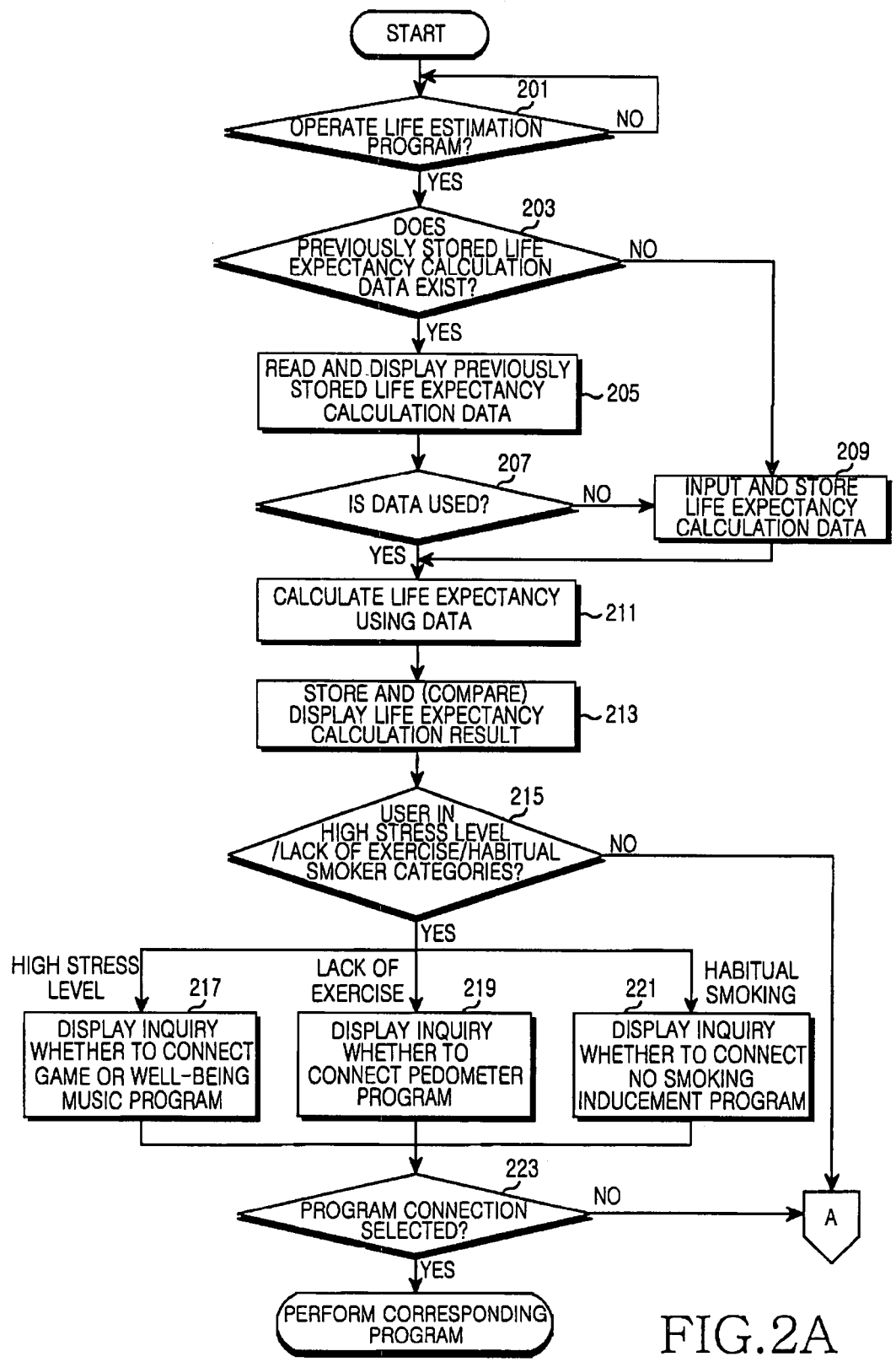
FIGS. 2A and 2B provide a flowchart illustrating a method for calculating life expectancy in a mobile communication terminal according to the present invention.
Figure 2B:
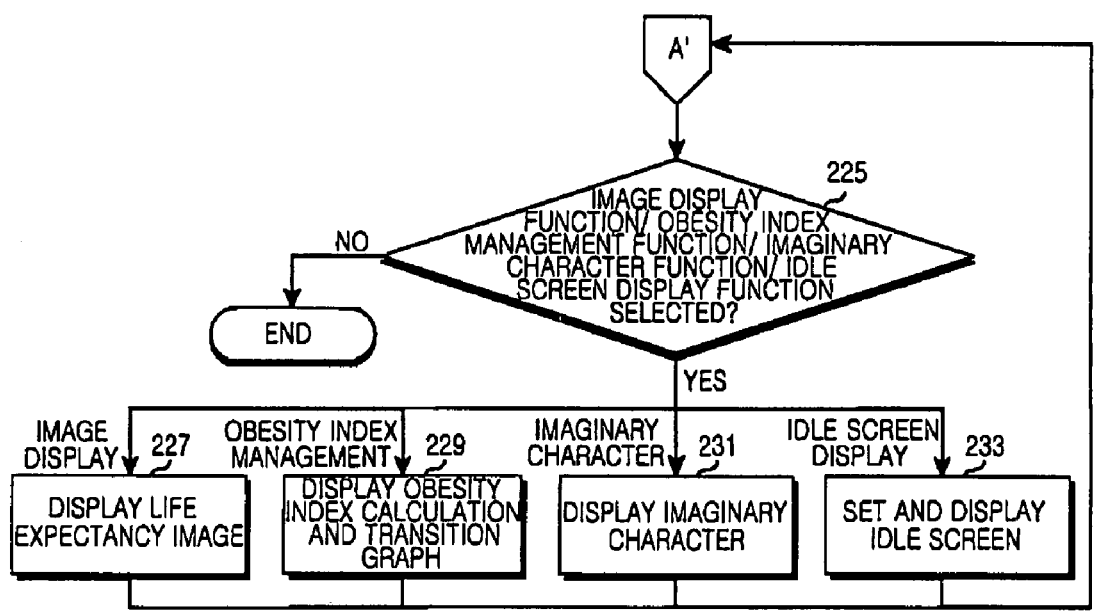

FIG. 2 is a flowchart illustrating a method for calculating life expectancy in a mobile communication terminal according to the present invention. Referring to FIG. 2, the control unit 101 determines whether a life expectancy program start menu is selected according to user key input in step 201. The life expectancy program start menu may be automatically operated at specific cycle times preset by the user, may be operated by the user receiving the program or may automatically operate when a life expectancy menu is not selected for a predetermined period of time. When the program is not operated during the specific cycle times, the program may be automatically operated or may be operated by the user receiving the program in order to provide continuous health care to the user. For example, a message window on which is written "Do you want to operate life expectancy program?" is displayed on an idle screen and the program may be operated by the user's selection.

When the life expectancy program start menu is selected in step 201, the control unit 101 determines whether previously stored life expectancy calculation data exists in step 203. The life expectancy calculation data is data utilized to calculate a user's life expectancy. The data includes data such as a user's present state, eating habits, exercise habits and environment. For example, the user's present state data may be data such as a user's gender, date of birth, height and weight.

When the previously stored life expectancy calculation data is determined to have been stored in step 203, the control unit 101 reads the life expectancy calculation data from the storage unit 107 and displays the read data on the display unit 105 such that the user confirms the data in step 205. The control unit 101 displays an inquiry for whether to use the displayed data on the display unit 105. The control unit 101 determines whether use of the displayed data is selected in step 207. When use of the displayed data is selected in step 207, the control unit 101 calculates the user's life expectancy using the read life expectancy calculation data in step 211.

When the previously stored life expectancy calculation data has not been stored in step 203 or the use of the displayed data is not selected in step 207, the control unit 101 modifies an operation mode of the terminal to a data input mode in step 209, receives the data for calculating the life expectancy, for example as shown in FIG. 3A, and stores the inputted data in the storage unit 107 using an inputted data. The control unit 101 calculates the user's life expectancy using the inputted life expectancy calculation data in step 211. Days lived and days yet to be lived of the user can be calculated on the basis of the calculated life expectancy result.

In step 213, the control unit 101 stores the calculated life expectancy result in the storage unit 107 as an inputted data and displays the calculated life expectancy result on the display unit 105 over a predetermined duration. For example, referring to FIG. 3B, the calculated life expectancy, days lived, and days to live can be displayed. When a previous life expectancy result is stored in the storage unit 107, the control unit 101 compares the previous life expectancy result to the calculated life expectancy result and displays the comparison result. To simplify a subsequent inputting process for the user, the inputted data is stored in the storage unit 107. Also, to compare the calculated life expectancy with a subsequent one, the calculated life expectancy result is stored.

In step 215, the control unit 101 determines whether the user has any symptoms through the calculated life expectancy result. Examples of such symptoms can include any symptoms that are determined using the life expectancy result, including a high level of stress, a lack of exercise and habitual smoking.

Figure 4A:
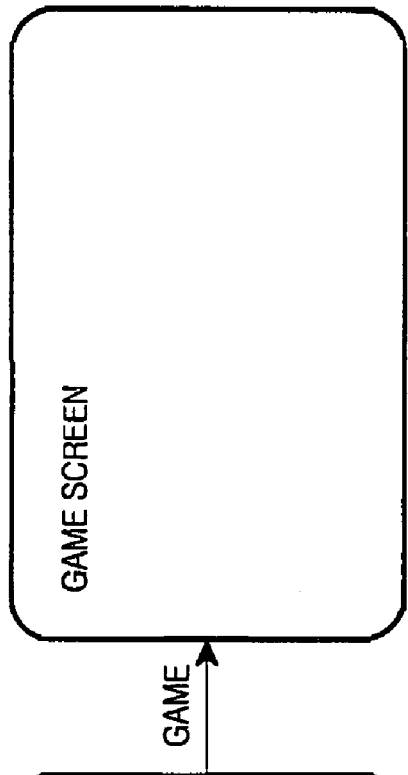
FIGS. 4A-4C are examples showing a program connected according to a life expectancy calculation result in the mobile communication terminal according to the present invention.
Figure 4B:
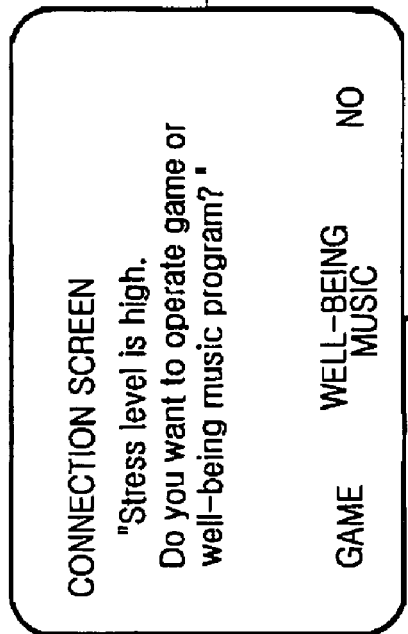
Figure 4C:
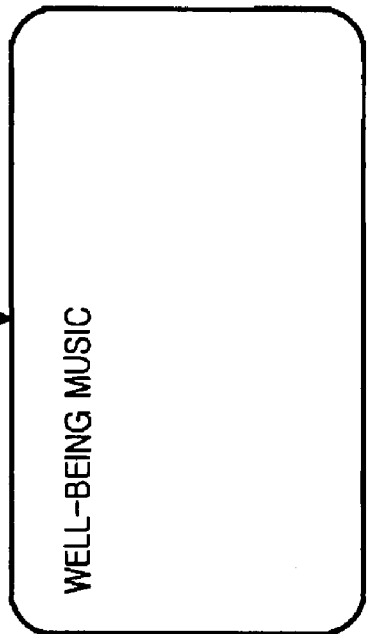

When the user is found to have high stress levels in step 215, the control unit 101 displays an inquiry as to whether a game or a well-being music program that reduces stress for the user should be connected in step 217. When the user is found to be under-exercised, the control unit 101 displays an inquiry as to whether a pedometer (e.g. a Ten thousand step pace checker) program linked a terrestrial navigation sensor should be connected in step 219. When the user is found to be a habitual smoker, the control unit 101 displays an inquiry as to whether a no-smoking inducement program should be connected in step 221. In step 223, the control unit 101 determines whether connection of a specific program is selected through a user's key manipulation in step 223. When the specific program is selected in step 223, a corresponding program is connected. Referring to FIG. 4b, a message window may display "Stress level is high. Do you want to operate game or well-being music program?" on the display unit 105. When the user selects the game, the game program is operated, as illustrated in FIG. 4B. When the user selects the well-being music, the well-being music program is operated, as illustrated in FIG. 4C.

When it is determined that the user has a low level of stress, or the user does not lack exercise, or the user is not a habitual smoker in step 215, or when the connection of the specific program is not selected in step 223, the control unit 101 determines whether a selection key for displaying a life expectancy image display function, an obesity index management function, an imaginary character function, or the life expectancy result on the idle screen has been inputted in step 225.

Figure 5:
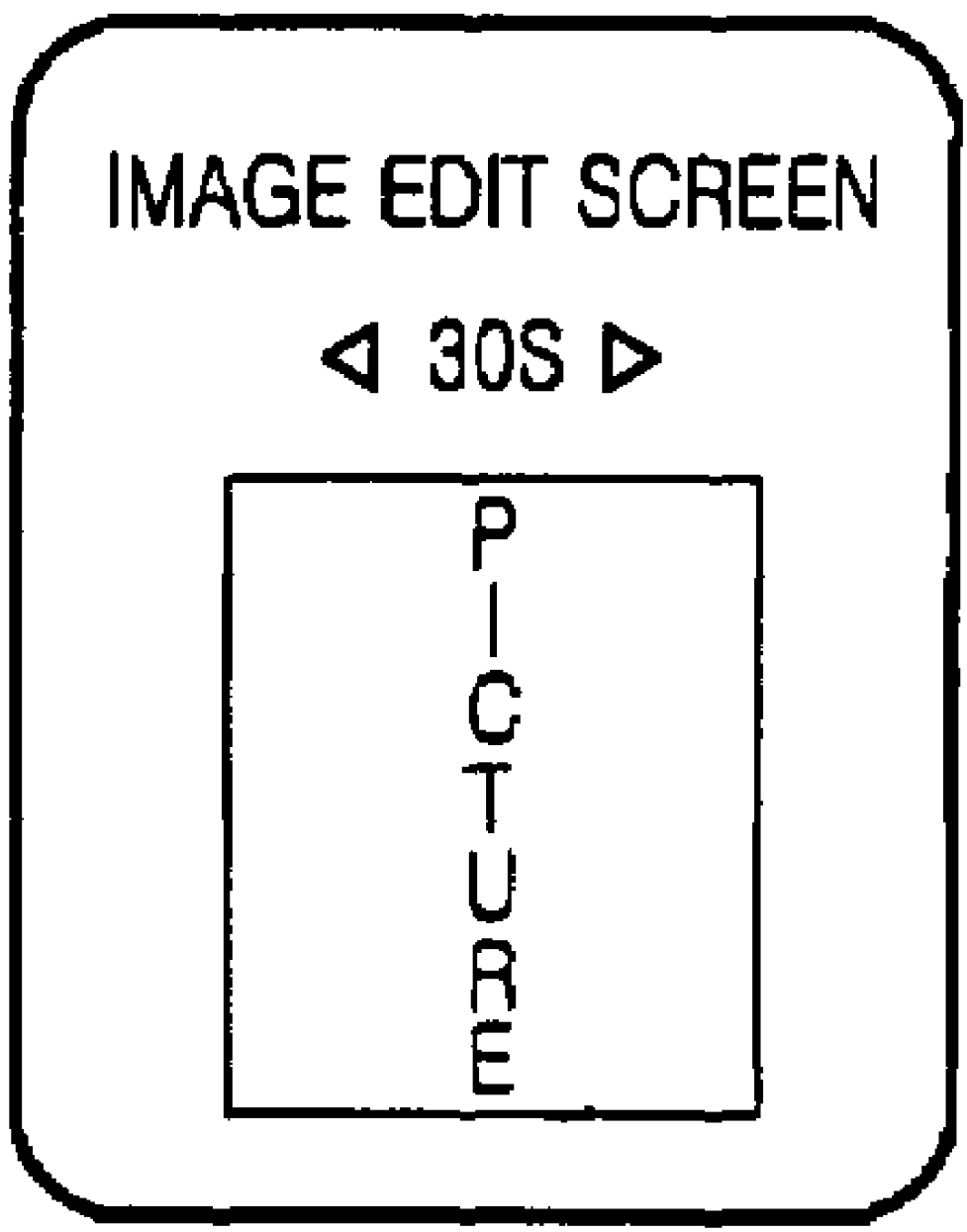
FIG. 5 is an example showing an image edit function according to a life expectancy calculation result in the mobile communication terminal according to present invention.

When it is detected that a key input has been made in step 225 for selecting the image display function during the projected life expectancy, the control unit 101 edits a previously inputted picture on the basis of an age range during the user's calculated life expectancy and displays the edited picture on the display unit 105 as a life expectancy image in step 227. Then, the control unit 101 returns to step 225. For example, as shown in FIG. 5, a corresponding age group and an image of the age group is displayed. The triangle shape displayed at either side of the age group is selected to change to an image corresponding another age group. To perform the image display function, a previously inputted picture must exist. The edited and inputted image may be set in a variety of screen modes according to the user's key operation and may be designated by a number inputted by the user. Examples of the screen may include the idle screen mode, a call receiving screen mode, a dialing screen mode, a wireless Internet connection screen mode, a turning off screen mode and a phone directory screen mode.

When the key for the selection of the obesity index management function is inputted in step 225, the control unit 101 calculates the user's obesity index using the inputted gender, height and weight, and displays the calculated result on the display unit 105 in step 229. Then, the control unit 101 returns to step 225. A date (e.g., from a few days, weeks, months, or years before) designated by the user using a previously stored input data can be displayed as a graph or a chart. When the user's obesity index is high, an increased lifespan expected in the case of normal weight and the life expectancy may be displayed.

When the key for the selection of the imaginary character function is inputted in step 225, the control unit 101 embodies an imaginary character on the basis of the data inputted by the user and displays the embodied imaginary character on the display unit 105 in step 231. Then, the control unit 101 returns to step 225.

When the selection key for displaying the life expectancy result on the idle screen is inputted in step 225, the control unit 101 sets the display of the life expectancy result on the idle screen in step 233 and displays the set result of the idle screen on the display unit 105. Then, the control unit 101 returns to step 225. Data corresponding to the life expectancy calculation result (e.g., life expectancy, age, days lived, days to live) can be displayed on the idle screen.

When none of the image display function during projected life expectancy, the obesity index management function, the imaginary character function, or display of the life expectancy result on the idle screen is inputted in step 225, the control unit 101 exits the life expectancy program, and the mobile communication terminal terminates the algorithm.

As described above, to further the current trend toward health and well-being, the mobile communication terminal that is always carried by its user provides a method for estimating remaining life expectancy. Therefore, the mobile communication terminal can manage the user's health and provide enjoyment through changing one's features to predict one's future appearance and connect a game at the same time. In addition, a user is encouraged to periodically use the program check the user's health and to reflect on one's previous lifestyle habits.

While the invention has been shown and described with reference to certain preferred embodiments thereof, it will be understood by those skilled in the art that various changes in form and details may be made therein without departing from the spirit and scope of the invention as defined by the appended claims.

What is claimed is:

1. A method for a mobile communication terminal calculating a life expectancy of a user, comprising the steps of:
   inputting user data when a life expectancy program menu is selected;
   operating a life expectancy program automatically when the life expectancy program menu is not selected for a predetermined period of time, and inputting the user data;
   calculating the life expectancy using the inputted user data; and
   displaying a calculated result on a display unit.

2. The method of claim 1, further comprising when the life expectancy program menu is selected,
   determining whether previously stored user data exists;
   reading the previously stored user data from a memory and displaying the read data on the display unit, when the previously stored user data is determined to exist; and
   calculating the life expectancy using the selected user data and displaying the calculated result on the display unit, when the read data is selected for use.

3. The method of claim 1, further comprising storing the inputted user data in a memory after the step of inputting user data.

4. The method of claim 1, further comprising storing a calculated result in a memory after the step of calculating the life expectancy.

5. The method of claim 1, wherein the user data is at least one of a user's gender, date of birth, height, weight, eating habits, exercise habits, and environment.

6. The method of claim 1, further comprising:
   comparing a previous life calculation expectancy result to the calculated life expectancy, when the previous life expectancy calculation result is determined to exist; and
   displaying a comparison result on the display unit.

7. The method of claim 1, further comprising:
   displaying an inquiry for connecting a program related to a corresponding symptom, when the calculated result does not satisfy a standard level corresponding to a specific symptom; and
   connecting a corresponding program, when connection of the program is selected.

8. The method of claim 7, wherein the specific symptom is at least one of stress, lack of exercise, and habitual smoking.

9. The method of claim 1, further comprising:
   displaying an inquiry for connecting a game or a well-being music program, when a stress level exceeds a standard level;
   displaying an inquiry for connecting a pedometer program, when an exercise level is less then a standard level; and
   displaying an inquiry for connecting a no-smoking inducement program, when a habitual smoking level is detected.

10. The method of claim 1, further comprising:
    editing a previously inputted picture image according to an age group, when an image display function is selected; and
    displaying the edited image on the display unit.

11. The method of claim 10, further comprising setting the displayed image for a corresponding screen.

12. The method of claim 11, wherein the corresponding screen is at least one of an idle screen, a call receiving screen, a dialing screen, a wireless Internet connection screen, a hanging up screen, and a phone directory screen.

13. The method of claim 10, further comprising transmitting the displayed image to a number inputted by a user when a transmission function is selected.

14. The method of claim 1, further comprising:
    calculating an obesity index using the inputted user data, when an obesity index management function is selected; and
    displaying the calculated obesity index on the display unit.

15. The method of claim 14, further comprising the steps of:
    storing the calculated obesity index; and
    displaying a transition graph or a chart using a previous obesity index calculation result and the calculated obesity index, when the previous obesity index calculation result is determined to exist.

16. The method of claim 14, further comprising:
    calculating an increased lifespan expected for a normal weight and associated life expectancy, when the calculated obesity index exceeds a predetermined level; and
    displaying the calculated increased lifespan and life expectancy on the display unit.

17. The method of claim 1, further comprising:
embodying an imaginary character based on the inputted user data, when an imaginary character function is selected; and displaying the embodied imaginary character on the display unit.

18. The method of claim 1, further comprising setting a display of the life expectancy calculation result on an idle screen when an idle screen display function is selected.

19. An mobile communication terminal for calculating a life expectancy of a user, comprising:

means for inputting user data;
means for receiving the user data, calculating the life expectancy using the inputted user data; and
means for outputting the calculated life expectancy result,
wherein the mobile communication terminal operates a life expectancy program automatically when the user does not select a life expectancy program menu for a predetermined period of time.

* * * * *